(12) United States Patent
Maissami

(10) Patent No.: US 8,584,301 B2
(45) Date of Patent: Nov. 19, 2013

(54) DENTAL DEVICE

(75) Inventor: Fari Maissami, Hinsdale, IL (US)

(73) Assignee: Denbur, Inc., Westmont, IL (US)

( * ) Notice: Subject to any disclaimer, the term of this patent is extended or adjusted under 35 U.S.C. 154(b) by 114 days.

(21) Appl. No.: 13/040,031

(22) Filed: Mar. 3, 2011

(65) Prior Publication Data

US 2012/0222229 A1 Sep. 6, 2012

(51) Int. Cl.
*A46B 1/00* (2006.01)
*A46B 9/04* (2006.01)

(52) U.S. Cl.
USPC ............................. 15/167.1; 15/187; 15/188

(58) Field of Classification Search
USPC ........................ 15/167.1, 187, 188; D4/128
See application file for complete search history.

(56) References Cited

U.S. PATENT DOCUMENTS

| 1,520,908 | A | * | 12/1924 | Meyer | 606/162 |
| 1,671,891 | A | * | 5/1928 | Dolan | 15/167.1 |
| 1,793,307 | A | * | 2/1931 | Dolan | 15/188 |
| 3,231,925 | A | * | 2/1966 | Conder | 401/268 |
| 5,028,077 | A | | 7/1991 | Hurst | |
| 6,049,934 | A | * | 4/2000 | Discko | 15/106 |
| 6,186,792 | B1 | | 2/2001 | Discko | |
| 6,241,408 | B1 | | 6/2001 | Lang | |
| 6,913,464 | B2 | | 7/2005 | Maissami | |
| D596,745 | S | | 7/2009 | Maissami | |
| D597,670 | S | | 8/2009 | Maissami | |
| D624,755 | S | * | 10/2010 | Luis et al. | D4/111 |
| D629,103 | S | | 12/2010 | Maissami | |
| 7,895,695 | B2 | * | 3/2011 | Bernini et al. | 15/104.94 |
| 2001/0054211 | A1 | | 12/2001 | Cabedo-Deslierres et al. | |
| 2004/0237233 | A1 | * | 12/2004 | Dragan et al. | 15/104.94 |
| 2006/0016033 | A1 | * | 1/2006 | Carpenter | 15/167.1 |
| 2009/0035727 | A1 | | 2/2009 | Maissami | |
| 2010/0051050 | A1 | | 3/2010 | Djang | |
| 2011/0143314 | A1 | | 6/2011 | Maissami | |

OTHER PUBLICATIONS

Co-pending Design U.S. Appl. No. 29/386,710, F. Maissami, filed Mar. 3, 2011.

* cited by examiner

*Primary Examiner* — Randall Chin
(74) *Attorney, Agent, or Firm* — Pauley Peterson & Erickson

(57) ABSTRACT

A dental device including an elongated handle and a tip portion formed at a distal end of the handle and tapering to a tip end. A plurality of bristles is integrally molded with the tip end from a flexible polymer material.

16 Claims, 2 Drawing Sheets

DENTAL DEVICE

BACKGROUND OF THE INVENTION

This invention relates generally to a dental device and, more particularly, to an anatomically sensitive endodontic applicator.

Applicators are widely used in the dental profession to apply dental compositions or other materials to a tooth surface or a tooth preparation. Applicators are also used to clean the excess materials surrounding a tooth preparation or inside a tooth preparation. Applicators may also be used to dry a tooth preparation. Such applicators are typically disposable. Many currently available applicators include fibrous strands at a tip of the applicator. The possibility of the fibers becoming separated from the applicator tip or becoming loose inside a tooth preparation is real. Fiber coating the fibers to the tip of an applicator is no guarantee that all fibers will remain on the tip of the applicator as materials are applied to a tooth preparation. In other words, as the applicator is dipped into the tooth preparation, or applied to the surface of a tooth preparation, fibers at the tip of the applicator may separate from the tip of the applicator. Some fibers may become loose and remain inside a tooth preparation. As a result, the loss of fibers inside a tooth preparation could be hazardous to the patient's health.

In view of the above, there is a continued need and a demand for an applicator with fibers that do not separate from the applicator.

SUMMARY OF THE INVENTION

The dental device according to this invention relates to a device and method for applying a dental composition or other material to a tooth surface or a tooth preparation. More particularly, this invention provides an applicator device that uses no fibers but instead has bristles formed from the plastic used to produce the handle of the device. The plastic is made of a rubberlike material in order to allow the bristles to be flexible, thus creating a brushlike applicator device. The applicator device of this invention provides a solution to the problem of fibers becoming loose from the flocked tip of current applicator devices when used within a tooth preparation, such as during a root canal or tooth implant procedure. The invention also provides a solution to the problem of fibers becoming separated from the applicator tip during shipping.

The general object of the invention can be attained, at least in part, through a dental device including an elongated handle and a tip portion formed at a distal end of the handle. The tip portion tapers to a tip end and at least one of the tip portion or the handle is formed of a flexible polymer material. A plurality of bristles at or near the tip end are also formed of the flexible polymer material.

The invention further includes a dental device including an elongated handle and a tip portion formed at a distal end of the handle and tapering toward a rounded tip end. A plurality of bristles is integrally formed with the rounded tip end, where the bristles and the rounded tip portion are formed from a flexible polymer material.

The invention still further includes a dental device including a tip portion, desirably tapered, and having a generally spherical tip end and a plurality of bristles radially extending from the tip end. The core and the bristles are integrally formed from a flexible polymer material. An elongated handle extends from the tip portion, and can be formed from the same polymer material, such as through an integral, one-piece molded product including the bristles, tip, and handle.

Other objects and advantages of this invention are apparent to those skilled in the art, in view of the following detailed description taken in conjunction with the appended claims and drawings.

DETAILED DESCRIPTION OF THE INVENTION

Figure 1:
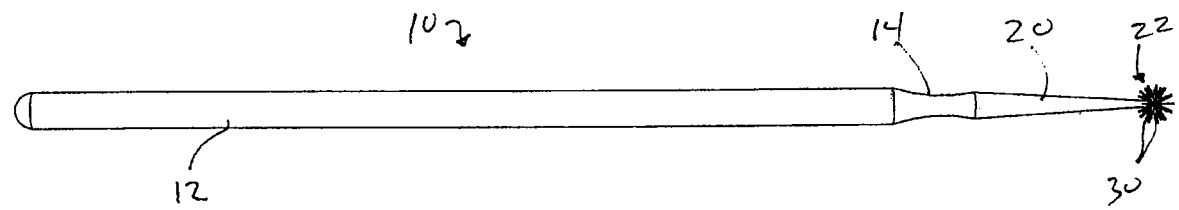
FIG. 1 is a side view of a dental tool, according to one preferred embodiment of this invention.
Figure 2:
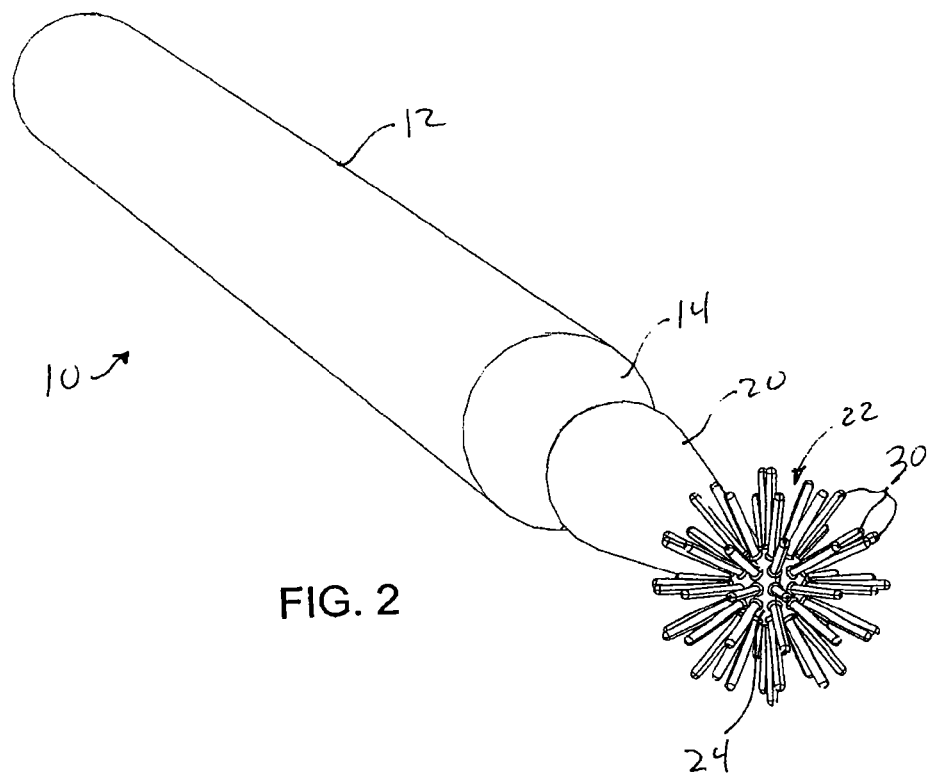
FIG. 2 is a side perspective view of the dental tool, as shown in FIG. 1.
Figure 3:
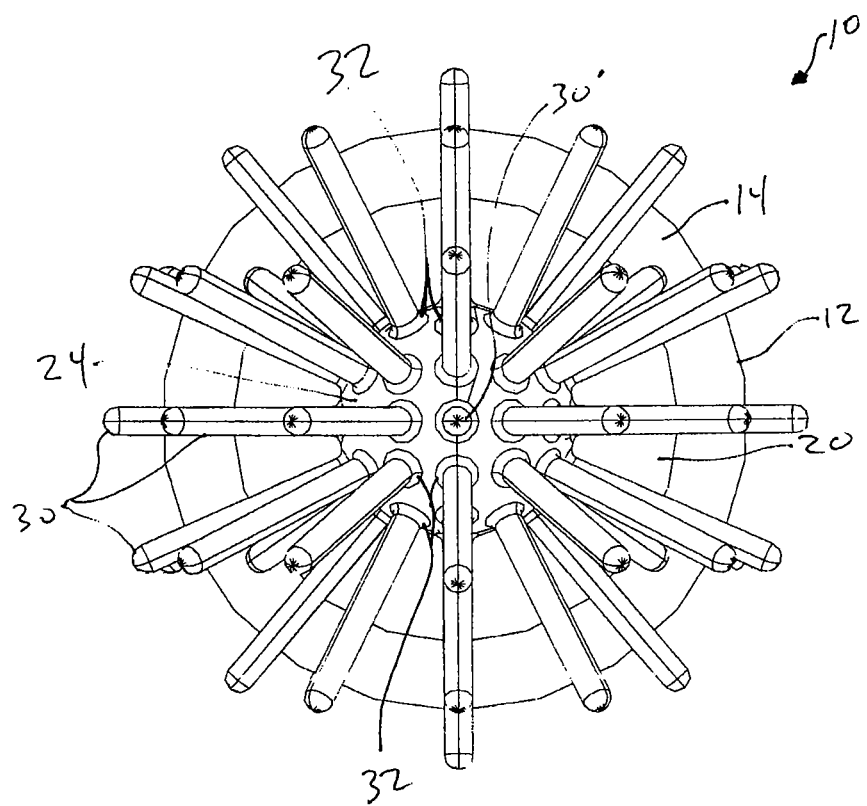
FIG. 3 is an end view of the dental tool, as shown in FIG. 1.

Referring to FIGS. 1-3 the present invention provides a dental device 10 that includes elongated handle 12 and a tip portion 20. The tip portion 20 is formed at a distal end of the handle 12 and has a tapered shape tapering to a smaller diameter tip end opposite the handle 12. The dental device 10 also includes an optional reduced diameter shoulder 14 formed between the elongated handle 12 and the tip portion 20. The shoulder 14 can facilitate gripping or holding of the handle 12 during use of the device 10. In one embodiment of this invention, the reduced diameter shoulder 14 can be formed to provide a weakened portion to permit a user to snap off the tip portion 20, from the handle 12. Such a separation permits a practitioner to choose a longer tool having an easier grip or a shorter tool having more maneuverability.

Various sizes, shapes, and configurations are available for the handle, tip portion, and shoulder. For example, the handle and/or tip portion can be square-shaped instead of tubular. The handle can also include flattened portions, ribs, or other grip patterns to promote grip during use. The shoulder 14 can also be formed at various positions along the handle 12, and can extend around a portion of or the entire circumference of the handle.

Various materials are available for use in forming the components of device 10. The dental device 10 is desirably formed of any suitable material that is generally flexible, sterile, nontoxic, and/or preferably inexpensive so as to promote disposability. In one embodiment of this invention, at least the tip portion 20 is formed of a flexible polymer material. The flexible polymer material can be any suitable plastic material known for forming dental applicators, and is desirably a rubber-like material that is semi-rigid but pliable. The handle is also desirably formed, at least in part, from the same material as the tip portion, and the dental device 10 is preferably formed in a unitary molded body, for instance, with an injection molded plastic construction. The tip portion 20, the shoulder 14, and/or the handle 12 may also be capable of being bent into and maintaining a desired position, preferably without instilling memory of the position to the device 10. Preferably, but not necessarily, at least a portion of the handle 12 and/or the tip portion 20 is made of a bendable material, such as a bendable plastic or metal material. Other suitable bendable materials known to those having ordinary skill in the art may be used to form dental device 10. In one embodiment of the invention, the tip portion 20 may include a combination of rigid and bendable materials.

Tip portion 20 is preferably tapered so as to, for example, facilitate use along gum lines or enable insertion into a tooth root during a root canal process. The taper preferably begins at handle 12 and tapers gradually to a tip end 22 that is opposite the handle 12. In such a manner, handle 12 may be manipulated so as to insert tip portion 20 into small spaces within the mouth.

As discussed above, according to one preferred embodiment of this invention, the dental device 10 includes a tip portion 20 that is freely pliable into a desired configuration. Specifically, tip portion 20 is preferably bendable with respect to elongated handle 12. In one preferred embodiment of this invention, the tip portion 20 is bendable and, specifically, pliable with respect to the elongated handle 12. Preferably, the dental device 10 is pliable to permit tip portion 20 to be bent in a desired position or configuration that permits access to a root canal.

The dental device 10 includes a plurality of bristles 30 at or near the tip end 22. The bristles 30 are desirably formed of the same flexible polymer material as the tip portion 20. In one embodiment of this invention, the bristles 30 are integrally formed with the tip end 22, thereby allowing the dental device 10 to be a single, integral device, such as made from an injection molding process. The integrally molded polymer bristles of this invention provide benefits over the separately frocked fiber bristles of currently available devices. By forming the bristles 30 as one-piece with the tip end 22, the invention reduces or eliminates the possibility of bristles falling off during use, which is a concern with fibrous bristles.

Various lengths, diameters, shapes, numbers, and placement configurations are available for the bristles of this invention, depending on need and the use of the dental device. In one embodiment of this invention, the tip end 22 is rounded and the bristles 30 radially extend from the rounded tip end 22. Each of the bristles 30 can be spaced apart from one or more adjacent bristles 30, such as shown in FIGS. 2 and 3, as desired or needed depending on the intended use.

In the embodiment shown in FIGS. 1-3, the rounded tip end 22 is formed as a sphere 24 at the tip end 22. The tip portion 20 tapers to a diameter that is less than a diameter of the sphere 24 connected thereto. The spherical tip end 22 thus forms a bristled ball at an end of the device 10. The bristles 30 radially extend from all sides of the sphere 24 in a spaced-apart placement. As best shown in FIG. 3, each of the bristles 30 extends outward from one of a plurality of opposing antipodal positions 32 on the surface of the sphere 24. In this configuration, most of the bristles 30 are configured as oppositely extending pairs of bristles. As shown in FIG. 3, at least one bristle does not have a corresponding oppositely extending bristle, namely the bristle 30' that extends opposite the tip portion 20 and parallel to a longitudinal axis of the handle.

The bristle-ball configuration shown in FIGS. 1-3, having bristles 30 extending from all sides of the spherical tip end 22, provides sufficient bristle placement for dental applications, however, as will be appreciated by those skilled in the art following the teachings herein provided, various and alternative sizes, shapes, and configurations are available for the rounded tip end and the bristles thereon. For example, the rounded tip end can be formed as other shapes such as, without limitation, a spheroid, an ellipsoid, or an ovoid, depending on need.

Thus the invention provides a dental device that is made from a flexible material, and preferably disposable, with a plurality of bristles formed in a manner that reduces the likelihood of bristle loss during use. The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A dental device comprising:
an elongated handle;
a tip portion integrally formed at a distal end of the handle, the tip portion tapering to a rounded tip end,
a plurality of bristles integrally formed with the tip portion, and each of the plurality of bristles extends radially from the rounded tip end; and
wherein the elongated handle, the tip portion and the plurality of bristles are all formed of a same flexible polymer material and integrally formed as a one-piece molded product.

2. The dental device of claim 1, wherein the rounded tip end comprises a sphere, a spheroid, an ellipsoid, or an ovoid.

3. The dental device of claim 2, wherein each of the bristles extends radially from the surface of the rounded tip end and is spaced apart from adjacent bristles.

4. The dental device of claim 1 further comprising a reduced diameter shoulder formed between the elongated handle and the tip portion.

5. The dental device of claim 1, wherein the tip portion is freely pliable.

6. The dental device of claim 1, wherein the tip portion is bendable with respect to the elongated handle.

7. A dental device comprising:
an elongated handle;
a tip portion formed at a distal end of the elongated handle, the tip portion tapering toward a rounded tip end,
a plurality of bristles formed of a same material as the elongated handle and integrally formed with the elongated handle and the tip portion, each of the plurality of bristles extends radially from the rounded tip end; and
wherein the elongated handle, the tip portion and the bristles are integrally formed as a one-piece molded product from a flexible polymer material.

8. The dental device according to claim 7, wherein an end of a tapered portion of the tip portion has a diameter that is less than the diameter of the rounded tip end.

9. The dental device according to claim 8, wherein the rounded tip end comprises a sphere, a spheroid, an ellipsoid, or an ovoid.

10. The dental device of claim 9, wherein each of the bristles extends radially from the surface of the tip end and is spaced apart from adjacent bristles.

11. The dental device of claim 9, wherein each of the bristles extend outward from one of a plurality of opposing antipodal positions on the surface of the tip end.

12. The dental device of claim 7, wherein each of the handle, the tip portion and the tip end are formed of the flexible polymer material.

13. A dental device comprising:
a tip portion including a generally spherical tip end and a plurality of bristles radially extending from the tip end, wherein the generally spherical tip end and the bristles are integrally formed from a same flexible polymer material using an injection molded plastic construction;
an elongated handle integrally formed with and extending from the tip portion; and
wherein the elongated handle, the tip portion and the plurality of bristles are integrally formed as a one-piece molded product.

14. The dental device of claim 13, wherein the tip portion tapers between an end of the handle to the spherical tip end.

15. The dental device of claim 13, wherein each of the bristles extend outward from one of a plurality of opposing antipodal positions on the surface of the spherical tip end.

16. The dental device of claim 15, wherein one of the bristles extends parallel to a longitudinal axis of the handle.

* * * * *